US011189366B2

(12) United States Patent
Lastinger et al.

(10) Patent No.: US 11,189,366 B2
(45) Date of Patent: Nov. 30, 2021

(54) FRAME OPTIMIZATION SYSTEM AND METHOD

(71) Applicant: ESSILOR INTERNATIONAL (COMPAGNIE GENERALE D'OPTIQUE), Charenton-le-Pont (FR)

(72) Inventors: John Lastinger, Dallas, TX (US); Gabriel Keita, Dallas, TX (US)

(73) Assignee: Essilor International, Charenton-le-Pont (FR)

( * ) Notice: Subject to any disclaimer, the term of this patent is extended or adjusted under 35 U.S.C. 154(b) by 640 days.

(21) Appl. No.: 15/565,915

(22) PCT Filed: Apr. 16, 2015

(86) PCT No.: PCT/IB2015/000851
§ 371 (c)(1),
(2) Date: Oct. 12, 2017

(87) PCT Pub. No.: WO2016/166566
PCT Pub. Date: Oct. 20, 2016

(65) Prior Publication Data
US 2018/0108436 A1    Apr. 19, 2018

(51) Int. Cl.
*G16H 10/60* (2018.01)
*G06F 16/9535* (2019.01)
(Continued)

(52) U.S. Cl.
CPC .............. *G16H 10/60* (2018.01); *A61B 3/00* (2013.01); *A61B 3/111* (2013.01); *A61B 5/1072* (2013.01);
(Continued)

(58) Field of Classification Search
CPC ........ G16H 20/13; G16H 40/60; G16H 20/00; G16H 30/40; G16H 10/60; G06Q 30/02;
(Continued)

(56) References Cited

U.S. PATENT DOCUMENTS

2004/0004633 A1    1/2004  Perry et al.
2010/0198381 A1    8/2010  Feldman
(Continued)

OTHER PUBLICATIONS

International Search Report, dated Dec. 9, 2015, from corresponding PCT/IB2015/000851 application.

*Primary Examiner* — Robert A Sorey
*Assistant Examiner* — Kimberly A. Sass
(74) *Attorney, Agent, or Firm* — Nixon & Vanderhye

(57) ABSTRACT

The disclosed embodiments include a system that has a processor for executing computer-executable instructions and a computer-readable storage media for storing the computer-executable instructions. These instructions, when executed by the processor, enable the system to receive prescription data of a patient for corrective lenses and image data associated with the face of the patient. The system is configured to determine lens attributes for the patient based upon the prescription data and also determine facial attributes of the patient from the image data. Based on the lens attributes and the facial attributes of the patient, the system determines at least one frame recommendation for the patient.

20 Claims, 5 Drawing Sheets

(51) Int. Cl.
*A61B 3/11* (2006.01)
*A61B 5/107* (2006.01)
*G06Q 30/02* (2012.01)
*A61B 3/00* (2006.01)
*G16H 40/60* (2018.01)
*G16H 20/00* (2018.01)
*G16H 30/40* (2018.01)
*G16H 20/13* (2018.01)
*G06K 9/00* (2006.01)
*G06Q 40/08* (2012.01)
*A61B 3/10* (2006.01)

(52) U.S. Cl.
CPC .......... *A61B 5/1077* (2013.01); *A61B 5/1079* (2013.01); *G06F 16/9535* (2019.01); *G06K 9/00275* (2013.01); *G06Q 30/02* (2013.01); *G06Q 40/08* (2013.01); *G16H 20/00* (2018.01); *G16H 20/13* (2018.01); *G16H 30/40* (2018.01); *G16H 40/60* (2018.01); *A61B 3/10* (2013.01)

(58) Field of Classification Search
CPC .......... G06Q 50/22; G06Q 40/08; A61B 3/00; A61B 5/1077; A61B 3/111; A61B 5/1072; A61B 5/1079; A61B 3/10; G06F 16/9535; G06K 9/00275
USPC ............................................................ 705/2
See application file for complete search history.

(56) References Cited

U.S. PATENT DOCUMENTS

| | | | |
|---|---|---|---|
| 2010/0281021 A1* | 11/2010 | Weeber ............ | B29D 11/00038 707/722 |
| 2013/0006814 A1* | 1/2013 | Inoue ...................... | A61B 3/111 705/26.81 |
| 2013/0088490 A1* | 4/2013 | Rasmussen ............. | G06T 17/00 345/421 |
| 2014/0257839 A1* | 9/2014 | Suter .................. | G06Q 30/0633 705/2 |

* cited by examiner

FRAME OPTIMIZATION SYSTEM AND METHOD

TECHNICAL FIELD

Embodiments of the invention are directed, in general, to providing a system and method for optimizing a frame for a patient based upon a patient's prescription and facial attributes.

BACKGROUND

Current dispensing techniques do not efficiently guide the dispensation of an appropriate frame tailored to a patient's facial anatomy. As a result, current techniques increase the risk that the performance of the selected lens will not achieve the desired vision correction for a patient. By accounting for the facial anatomy of the patient, the practitioner will be able to better select the appropriate frame needed for the patient.

Additionally, in the majority of the cases, the patient's full prescription is not accounted for in the frame selection process. For example, a patient will fruitlessly spend time selecting a frame that he/she likes only to find out that the selected frame will not work for the patient's prescription. Additionally, even if the selected frame will work with the patient's prescription, it may not provide the optimum vision correction. For instance, in order to optimize the performance of the selected lens, the frame must be of sufficient size and depth to accommodate the lens prescription and material required to be manufactured by the practitioner. Aspects of prescriptions such as power, sphere, and cylinder may all impact the optimal size, shape, and material of lenses for a particular patient and therefore the frames best suited for use with such lenses.

In accordance with the disclosed embodiments, by accounting for both the facial anatomy of the patient, and the prescription written by the doctor, the frame and lens selection process will be optimized to deliver the highest possible visual performance to the patient and at the same time, reduce the amount of time spent selecting a frame.

SUMMARY OF THE INVENTION

The disclosed embodiments include a system that is used to determine at least one frame recommendation for a patient based upon the prescription data of a patient and the facial attributes of the patient. In certain embodiments, this may be a specially configured machine that may include an integrated facial imaging device or scanner and may also include a three-dimensional printer, or related technology, for automatically creating a selected frame or a selected frame and lens combination based on the at least one frame recommendation.

As an example, in one embodiment, the disclosed system includes a processor for executing computer-executable instructions and a computer-readable storage media for storing the computer-executable instructions. These instructions when executed by the processor enable the system to perform features including receiving prescription data of a patient for corrective lenses; receiving image data associated with the face of the patient; determining lens attributes for the patient based upon the prescription data of the patient; determining facial attributes from the image data of the patient; and determining at least one frame recommendation for the patient based upon the lens attributes and the facial attributes of the patient.

BRIEF DESCRIPTION OF THE DRAWINGS

For a more complete understanding of the description provided herein and the advantages thereof, reference is now made to the brief descriptions below, taken in connection with the accompanying drawings and detailed description, wherein like reference numerals represent like parts.

DETAILED DESCRIPTION

Figure 1:
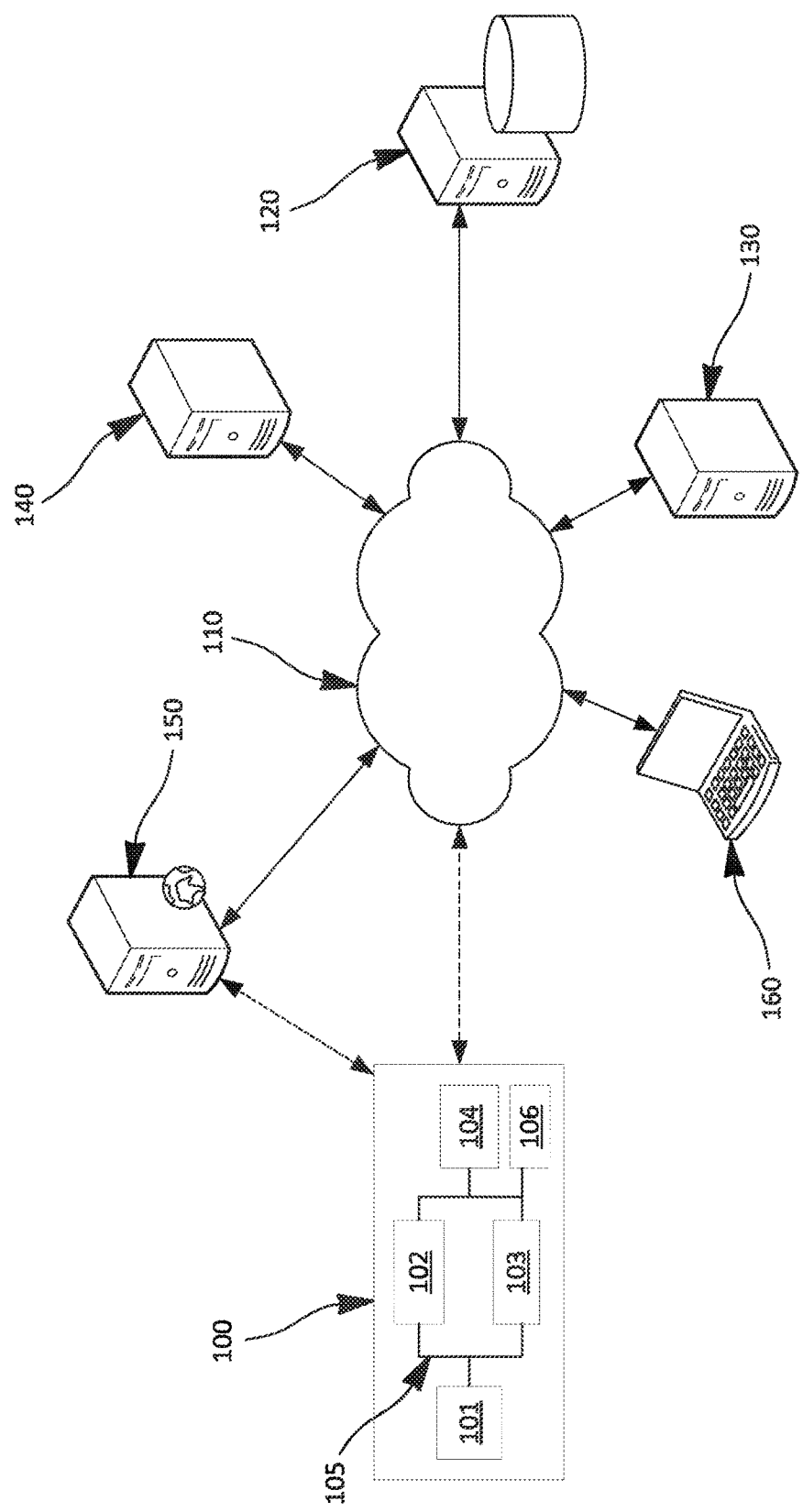
FIG. 1 illustrates a frame and lens optimization system 100 according to one embodiment.

In the description which follows the drawing figures are not necessarily to scale and certain features may be shown in generalized or schematic form in the interest of clarity and conciseness or for informational purposes. In addition, although making and using various embodiments are discussed in detail below, it should be appreciated that as described herein are provided many inventive concepts that may be embodied in a wide variety of contexts. Embodiments discussed herein are merely representative and do not limit the scope of the invention.

FIG. 1 illustrates a frame and lens optimization system 100 according to one embodiment. In the depicted embodiment, the frame and lens optimization system 100 communicates with a number of other devices including, but not limited to, a frames database 120, a frames/lens fulfillment system 130, and a billing/insurance system 140 over a communication network 110.

The communication network 110 may be any type of wired or wireless connection, which may include one or more public or private networks or some combination thereof, such as the Internet, an intranet, a mobile cellular or data network, or any other network operable to transmit data to and from the frame and lens optimization system 100.

In one embodiment, the frame and lens optimization system 100 comprises components including one or more processors 101, a computer-readable storage media 102, an input/output interface 103, and a network interface 104. Each of the components of the frame and lens optimization system 100 communicates via a systems bus 105 that transfers data between the components. The processors 101 are configured to process data and execute computer-executable instructions. These instructions may include, but are not limited to, machine code instructions, bytecode for a software interpreter, object code, and source code in a high-level programming language.

Data and computer-executable instructions are stored in the computer-readable storage media 102. The computer-readable storage media 102 may be any appropriate memory device or computer storage media, such as, but not limited to, a hard disk drive, random access memory, read only memory, electrically erasable programmable read-only memory, flash memory or other memory technology, compact disc—read only memory, digital versatile disks or other optical disk storage, magnetic cassettes, magnetic tape, magnetic disk storage or other magnetic storage devices.

The input/output (I/O) interface 103 comprises an input interface for receiving user input or data from one or more peripheral devices. For example, the I/O interface 103 may receive user input or data from one or more input devices such as, but not limited to, a keyboard, mouse, touch screen, microphone, scanner, and/or a camera. The I/O interface 103 also comprises an output interface for outputting information to one or more device or component associated with the frame and lens optimization system 100. For example, the I/O interface 103 may output data or other information to a display device for displaying information to a user, another system, and/or to a printer for printing a recommended frame.

As mentioned above, the frame and lens optimization system 100 may also include network interface 104 for enabling the frame and lens optimization system 100 to send and receive data over the network 110. The network interface 104 may include one or more wired or wireless interfaces such as, for example, an Ethernet port or a wireless transceiver and is not limited to any particular communication protocol. For example, in one embodiment, as will be further described herein, the frame and lens optimization system 100 may query or communicate with a frames database/system 120 that contains data on a plurality of frames for retrieving one or more recommended frames for a patient based upon the patient's prescription and facial anatomy. Non-limiting examples of frame data that may be stored in the frames database 120 include the AB/DBL frame measurements, where A is the distance across the center of one lens, B is the height of the lens, and DBL is the bridge size or the distance between the lenses. Frame data may also include: frame width; wrap angle, pantascopic tilt in reference to a vertex distance, temple length; bridge width, bridge type such as a keyhole or saddle style; whether the frame includes nose pads; rimmed/rimless lenses; spring-hinged; temple tips; flexibility/adjustability range; frame color; frame material such as plastic—cellulose acetate, propionate, nylon or metal—titanium, stainless, or nickel; cost; manufacturer; durability rating; current promotions; in stock/out of stock; and ordering lead time. The frame data may also indicate ranges corresponding to measurements of facial attributes. For example, a particular frame may have a temple width range corresponding to a forehead width of a patient indicating that it is suitable for temple-to-temple measurements of between 12.5 and 14 centimeters. The frame may also have a temple length range corresponding to a distance from the forehead to behind the ear of a patient of between 10.5 and 12 centimeters. Such ranges may be used to quickly identify potential frames suitable for particular patients as further described below.

The frames database 120 may be a combination of one or more private or public database, one or more websites, and/or any other system or data repository containing data related to a plurality of frames. The frames database 120 may contain information provided and/or maintained by a single vendor, combination of vendors, or an independent third party. In some embodiments, the frames database 120 may be provided and/or maintained by a provider of the frame and lens optimization system 100, Still, in certain embodiments, the frame and lens optimization system 100 may locally store the frames data in a local data storage unit or database.

In some embodiments, the network interface 104 may also enable the frame and lens optimization system 100 to communicate directly with one or more devices. For example, in certain embodiments, the frame and lens optimization system 100 may communicate with a web server 150 for providing the services disclosed herein as a web application or website to one or more remote clients 160. In some embodiments, the frame and lens optimization system 100 may communicate with a web server 150 for retrieving data from one or more websites. Still, in certain embodiments, the frame and lens optimization system 100 may provide services to the one or more remote clients 160 directly without the use of the web server 150. In some embodiments, the frame and lens optimization system 100 may be a standalone machine that is not connected to any communication network. Further, in some embodiments, the frame and lens optimization system 100 may be a portable or mobile device.

As mentioned above, examples of other devices that the frame and lens optimization system 100 may communicate with include, but are not limited to, the frames/lens fulfillment system 130 and the billing system 140. For instance, in one embodiment, once the frame and lens optimization system 100 performs one or more of the processes disclosed herein for providing at least one recommended frame, the frame and lens optimization system 100 may be configured to communicate with the frames/lens fulfillment system 130 to order, separately or in combination with lenses, a selected frame. Additionally, in some embodiments, the frame and lens optimization system 100 may be further configured to communicate with the billing system 140 for billing at least a portion of the order or rendered services to an insurance company.

In some embodiments, the frame and lens optimization system 100 may also be specially configured to include one or more optional components 106 including but not limited to, one or more digital cameras, a facial scanner, and/or a three-dimensional 3D printer. The one or more optional components 106 may be integrated within the frame and lens optimization system 100 or coupled to the frame and lens optimization system 100. For example, it is envisioned that the disclosed embodiments include a specially configured machine at an eye doctor's office or stand-alone kiosk that includes a built-in facial image scanner that is able to scan and generate at least a digital image of a patient's front and lateral facial dimensions. In certain embodiments, the specially configured machine may also execute instructions for three-dimensionally printing at least one of the recommended frames as described herein. In some embodiments, the prescription lenses may also be printed alone and/or in combination with at least one of the recommended frames.

Figure 2:
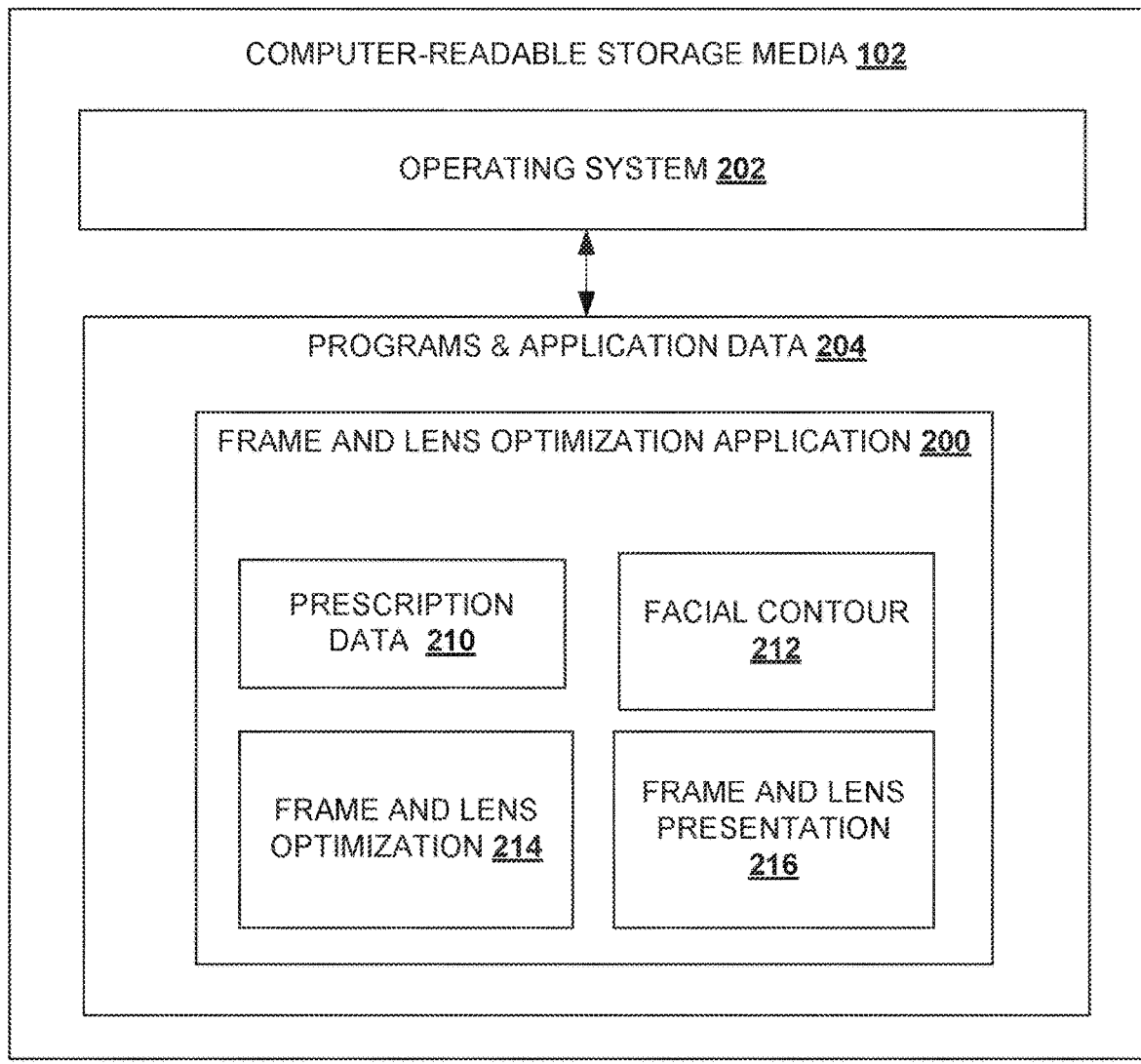
FIG. 2 is a block diagram of an example embodiment of a frame and lens optimization application 200.

FIG. 2 is a block diagram of an example embodiment of a frame and lens optimization application 200. The frame and lens optimization application 200 comprises of data and computer executable instructions stored in the computer-readable storage media 102, such as main memory or a hard drive, that when executed performs the processes disclosed herein. In some embodiments, some or all of the data and/or computer executable instructions of the frame and lens optimization application 200 may be downloaded or retrieved over the communication network 110 to one or more systems. In certain embodiments, the computer-readable storage 102 media may also store data and computer executable instructions associated with an operating system 202 and/or one or more programs/applications 204.

In the depicted embodiment, the frame and lens optimization application 200 includes examples of the types of classes, objects, or software modules that may be employed to perform the processes disclosed herein. For instance, in one embodiment, the prescription data module 210 may include computer executable instructions for generating a graphical user interface comprising of input fields for receiving prescription data user input. The prescription data specifies the value of all parameters the prescriber has deemed necessary to construct and/or dispense corrective lenses appropriate for a patient. The distant vision (DV) portion of the prescription describes the corrections for seeing far away objects. The near vision (NV) portion is used in prescriptions for bifocals to see very close objects. Non-limiting examples of prescription data includes a spherical correction parameter value for correcting the refractive error of the eye with a single convergent or divergent refractive power in all meridians, a cylindrical correction parameter value for correcting astigmatic refractive error of the eye by adding or subtracting power cylindrically in a meridian specified by the prescribed axis; and an axis parameter value that indicates the angle in degrees of one of two major meridians the prescribed cylindrical power is in. In some embodiments, the prescription data module 210 may include computer executable instructions for retrieving the prescription data from an external system that stores the prescription data.

The facial contour image module 212 may include computer executable instructions for controlling one or more imaging devices such as, but not limited to, one or more cameras, scanners, or any other type of imaging device for capturing image data associated with the face of the patient and determining the facial attributes of a patient. For example, in one embodiment, the facial contour image module 212 may include instructions for capturing at least one frontal view and at least one lateral view image of the patient's head. In some embodiments, the facial contour image module 212 includes instructions for performing a full scan and/or capturing a plurality of images that enables all or substantially all facial attributes of the patient to be determined. For instance, in certain embodiments, the facial contour image module 212 includes computer executable instructions are for determining one or more of the following facial attributes: temple-to-temple width, temple length, nose dimensions, inter-pupillary distance, or the shape of a face such as round, oval, diamond, oblong, square, triangular, pear-shaped, rectangular, or heart-shaped. Other facial attributes that may also be determined include skin tone, eye color, and hair color. For instance, cool skin or warm skin tones can influence the choice of frame and lens. For example, certain eye colors may benefit from having certain lenses or coating, which in turn may affect frame choices. Additionally, certain frame colors or style may appear more pleasing with certain eye color, hair color, or even hair style.

In one embodiment, the shape of the face may be determined by facial contour module 212 by measuring the width of the forehead, the width of the cheek bone, and the width of the jaw-line observed in the frontal view of the patient's head. The shape of the face may be further determined by measuring the distance between a patient's forehead, cheek bone, and jaw-line. The facial contour module may also capture additional patient information relevant to frame selection such as hair and eye color and skin tone.

In certain embodiments, the facial contour image module 212 may include computer executable instructions for retrieving statistical data associated with a patient's ethnicity, height, weight, or any other characteristic associated with the patient. The statistical data may assist in determining any of the above described facial attributes of the patient.

Additionally, in some embodiments, the facial contour image module 212 further includes computer executable instructions for generating a three-dimensional image of the patient's head/face based on the determined facial attributes. In certain embodiments, the three-dimensional image may be used for displaying one or more recommended frames for enabling a patient to view a selected frame on his or her own image.

In one embodiment, a frames and lens optimization module 214 may be provided to include computer executable instructions for determining lens attributes for the patient based upon the prescription data of the patient. Non-limiting examples of lens attributes include material, coatings, including, but not limited to, scratch resistance coatings, polarization, self-healing, bi-focal, size, shape, curvature, photochromic, electrochromic, tinting, the relationship between smudge and curvature (smudge visibility the visibility of smudge based on the curvature of the lens), filters, and thickness.

Additionally, in certain embodiments, the frames and lens optimization module 214 may include computer executable instructions for receiving one or more patient attributes and using the patient attributes in conjunction with the prescription data for determining the lens attributes for the patient. The patient attributes may include, but are not limited to, age, skin tone, ethnicity profile, medical history/profile/patient's familial medical history, DNA testing, anatomical/anthropomorphic profile of a patient's face, vocation, previous eyewear data (data on frames and lenses previously selected or worn by patient), susceptibility to eye strain, recreation, or daily activities such as the average time spent in front of a computer, reading, or other routine activities that may impact lens selection. In certain embodiments, the patient's mood may be a contributing patient attribute. For example, certain colors or the amount of light that a patient receives could impact a patient's emotions. For instance, for some patients that live in northern climates where the amount of sunlight is limited, a certain lens or a filter to a lens may be selected to let in more light in the winter to enhance mood. In one embodiment, electrochromic lens having one or more sensors on the lens could be used to enhance the light to affect a patient's mood. In some embodiments, the patient attributes may be retrieved from an external source. For instance, in one embodiment, the patient attributes may be retrieved from a patient's social networking site, patient intake form, electronic medical record, or other suitable source.

The frames and lens optimization module 214 further includes computer executable instructions for determining at least one frame recommendation for the patient based upon the lens attributes and the facial attributes of the patient. In one embodiment, the computer executable instructions are configured to simply output the frame dimensions of the at least one frame recommendation. In other embodiments, the computer executable instructions may also be configured to generate an image of at least one frame recommendation for the patient. Still, in some embodiments, an image of the at least one frame recommendation may be retrieved from an external source, such as, but not limited to, a database or a website. For example, in one embodiment, in determining the at least one frame recommendation for the patient based upon the lens attributes and the facial attributes of the patient, the frames and lens optimization module 214 may include instructions for querying a remote database containing frame information such as frames database 120 as described above.

In one embodiment, once the at least one frame recommendation for the patient is determined, the frame and lens optimization application 200 may employ a frames and lens presentation module 216 that includes instructions for displaying and filtering the at least one frame recommendation for the patient based on one or more frame criteria. For example, the at least one frame recommendation may be filtered based on a patient's preference for a particular brand, vendor, style, color, material, cost, available inventory, durability/flexibility of the frame, weight and pressure distribution of the frame and lens in relation to the patient's head, optimal bend/angle of the frame/lens in relationship to the patient's face, elasticity of the skin as an indication of the ideal weight/pressure distribution of the lens/frame to the lens, as potentially influenced by lifestyle, measuring the elasticity of skin and/or any insurance coverage (e.g., wholly, partially, or not covered at all). Similarly, the at least one frame recommendation may be filtered based on the doctor's preference for one or more of the above factors or other factors. Further, each of the above preferences may be given a weight based on level of importance. For example, in one embodiment, the weighting of the preferences may be indicated as being: required, strong positive preference, slight positive preference, no preference, strong negative preference, slight negative preference, not acceptable. For instance, whether a frame is covered by insurance may be specified as being an absolute requirement.

In some embodiments, the frames and lens presentation module 216 includes instructions for different display options for the at least one frame recommendation. For example, in one embodiment, the at least one frame recommendation may be shown as two dimensional images, three dimensional rotatable images, displayed on an image of the patient, or displayed on images of other people that are determined to have similar facial attributes as the patient.

In certain embodiments, the frames and lens presentation module 216 may also include computer executable instructions for printing a selected frame from the at least one frame recommendation using a three-dimensional printer. In some embodiments, the instructions for printing a particular frame may be retrieved or downloaded from an external source such as a website or the frames database 120. The frames and lens presentation module 216 may also include the computer executable instructions for initiating a transaction to purchase a selected frame from the at least one frame recommendation. Further, in some embodiments, the frames and lens presentation module 216 may include computer-executable instructions for billing at least a portion of the transaction to an insurer of the patient.

Figure 3:
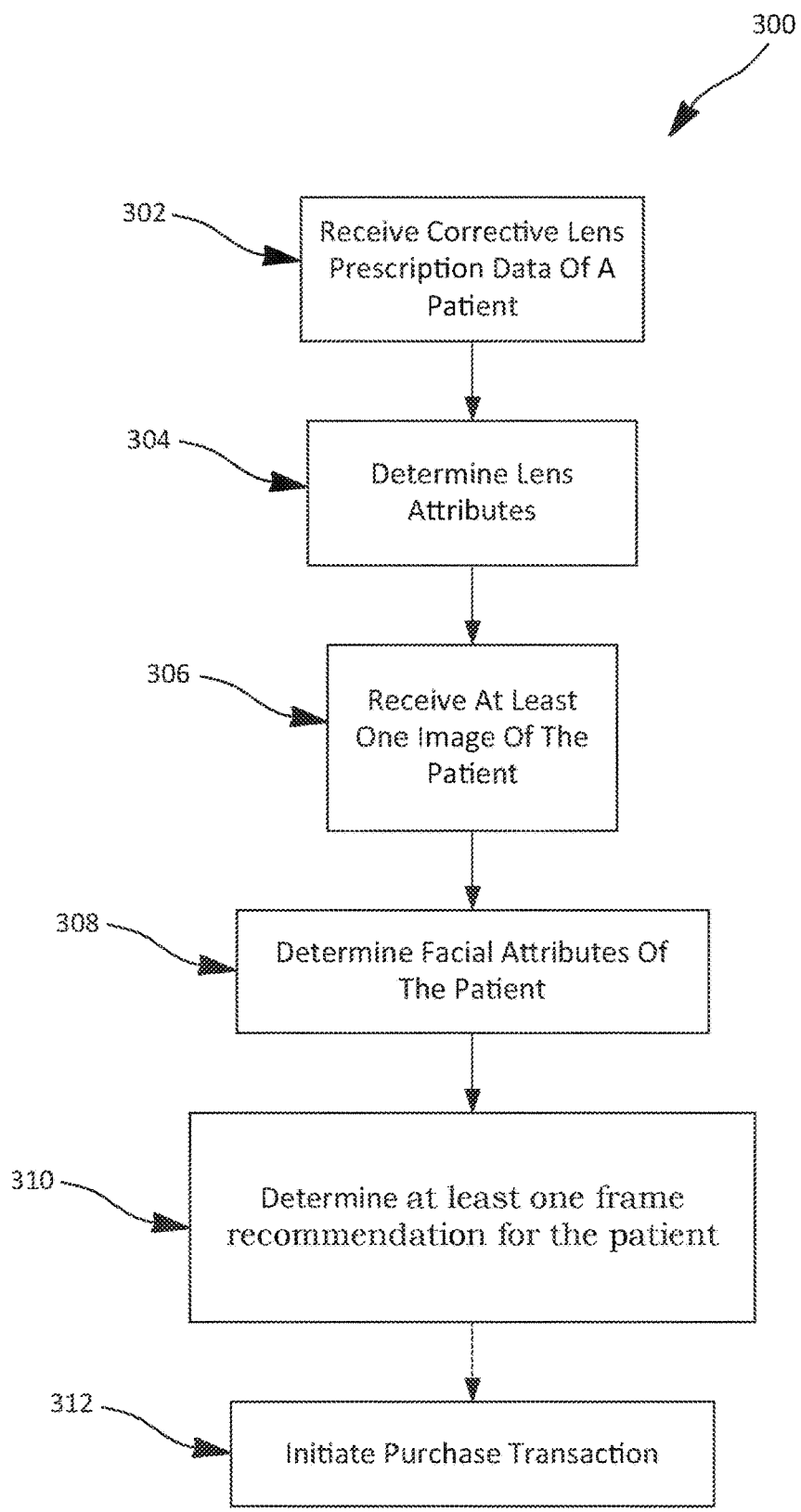
FIG. 3 is a flowchart illustrating a process 300 for determining at least one frame recommendation for the patient in accordance with one embodiment.

FIG. 3 is a flowchart illustrating a process 300 for determining at least one frame recommendation for the patient in accordance with one embodiment. The process begins by receiving corrective lens prescription data of a patient at step 302. As described above, the prescription data may be manually entered by a user or may be imported from another system. Other patient attributes as previously described may also be received by the system. At step 304, the process determines the patient's lens attributes based at least on the prescription data of the patient, and patient attributes if any.

The process at step 306 receives image data associated with the face of the patient to determine facial attributes of the patient at step 308. In certain embodiments, the process may include generating a three-dimensional image of the patient for determining the facial attributes.

Based on the lens attributes and the facial attributes, the process at step 310, determines at least one frame recommendation for the patient. As stated above, this step may involve outputting the appropriate frame dimensions for the patient and/or may involve querying a local or remote database containing frame information for determining at least one recommended frame for the patient. For instance, in one embodiment, as will be further described in FIG. 4, a plurality of frames may be broken up into a number of subset of frames such as frames having frame dimensions satisfying a particular range and based on the patient's lens attributes and facial attributes, the optimum frames for the patient would be found in a particular subset of frames.

Alternatively, in other embodiments, exact dimensions or a particular range of dimensions are queried, and frames satisfying the query requests are returned as recommended frames for the particular patient. For example, in one embodiment, the process may query for all frames having a 51 mm lens diameter, an 18 mm bridge width, and 140 mm temple arm length. In some embodiments, the process may be configurable to return frames having a±X mm from one or more of the inputted values. For instance, in the above example, the temple length can be adjusted to return frames having ±2 mm of 140 mm, while the other parameter values remain the same or they may also be adjusted. Other parameters may also be included be included in a query includes total width, which is the distance from the extreme left to the extreme right of the frame from a full frontal view, or height, which is the distance from top of lens area to the bottom.

In certain embodiments, the process at step 312 may also be configured to initiate a purchase transaction for the lens, a particular recommended frame, or a combination of both. In some embodiments, the process may also be configured to bill at least a portion of the provided services or purchase transaction to an insurance company of the patient.

Figure 4:
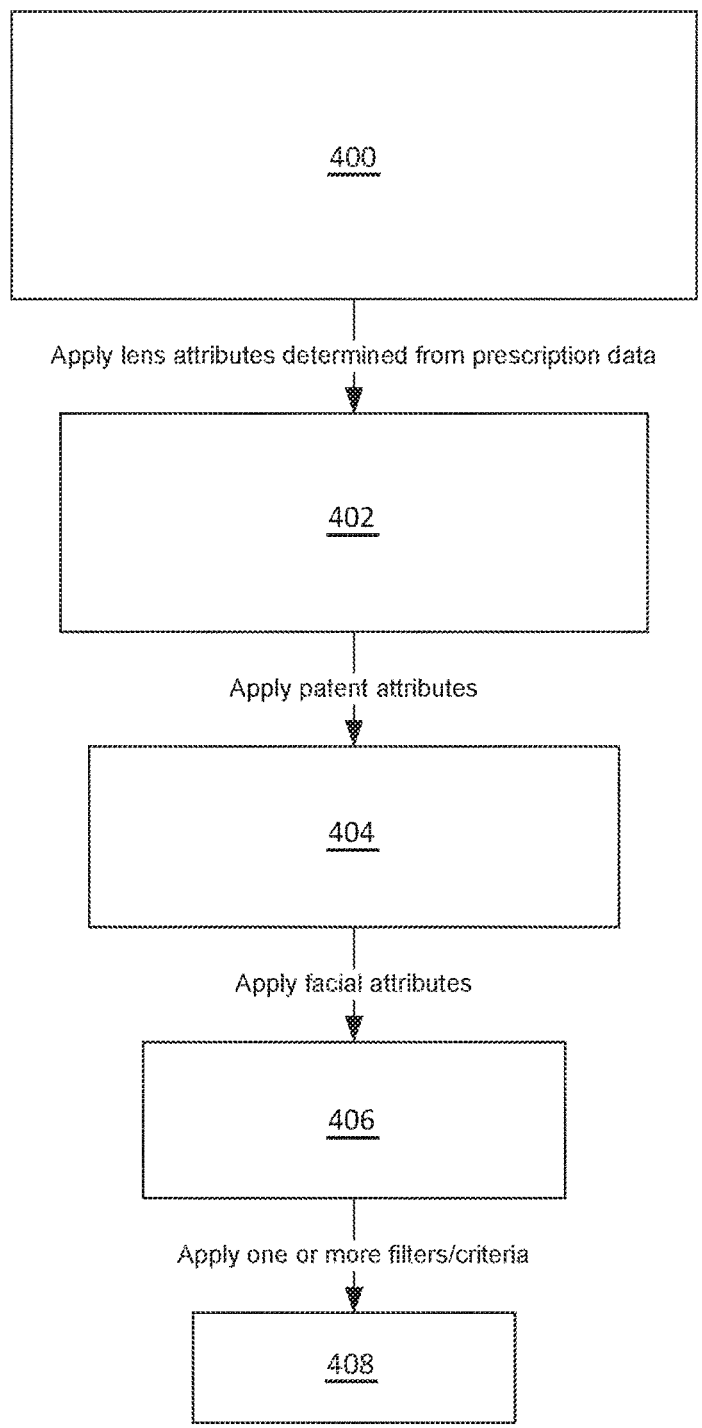
FIG. 4 is a flowchart illustrating a process for providing at least one recommended frame in accordance with one embodiment.

FIG. 4 is a flowchart illustrating a process for providing at least one recommended frame in accordance with one embodiment. The process begins at frames set 400, which contains information on all available frames in a frames database. The process applies the lens attributes determined from the patient prescription data to generate a subset of frames based on the lens attributes at frames set 402. For example, the lens attributes could include a lens thickness. Thus, only frames capable of supporting the specified lens thickness will be part of the frames set 402. Other lens attributes could include contour, optimal viewing area or size, and bifocal capability that may drive specific frame choices. In some embodiments, the process will select only frames that match all specified lens attributes. Alternatively, in some embodiments, if no frames match all lens attributes, the process may select the frames that satisfy the most lens attributes. Still, in some embodiments, the process may apply a greater weight to a particular lens attribute compared to other attributes. For example, in one embodiment, the process may apply the greatest weight to the contour of the lens to ensure that all selected frames at least support the shape of lens that provide the optimum viewing experience for a patient.

From frames set 402, the process applies the patient attributes to generate a smaller subset of frames at frames set 404, which satisfies the patient attributes and lens attributes. As stated above, patient attributes may include skin tone, lifestyle, and personality. For example, for warm complexions such as yellow, bronze or golden cast skin, generally contrasting colors as pastels, white, and black frames should be avoided. Instead, the best frame colors for a person with a warm complexion are light tortoise, browns shades, gold or honey, beige, and olive green. If the patient has a cool complexion, e.g., skin has pink or blue undertones, colors that wash out the face should be avoided. Instead, for patients with cool complexions, the process may be configured to select frames that are silver, black, dark tortoise, pink, purple, blue, mauve and gray.

Regarding lifestyle and personality, for professionals, the process may select sensible styles, whereas for adventurists or gamers, the process may select more stylish/trendy frames or frames that enhance the adventure or gaming experience. Again, in some embodiments, particular patient attributes may be weighted higher than other patient attributes. Similarly, in some embodiments, certain lens attributes may outweigh any patient attribute as optimal viewing enhancement may be preferred over style. For example, in one embodiment, a patient attribute that conflicts with the appropriate frame dimensions needed to support a particular lens attribute that affects a patient's prescription will be removed or disregarded in the determination of the recommended frames.

The process then further comprises applying the facial attributes to frames set 404 to further reduce the subset of frames to at least one recommended frame at frames set 406, which satisfies the patient attributes, lens attributes, and facial attributes. Similar to the other attributes, in some embodiments, certain facial attributes may be assigned a greater weight than other facial attributes, patient attributes, and in some cases, lens attributes. As an example, one important facial attribute is the shape of the patient's face such as, but not limited to, round, oval, square, diamond or heart-shaped. Examples of rules that the process may apply regarding this facial attribute may include: 1) for round shaped faces, select square or rectangular shaped frames as they enhance the face by making it appear slimmer and longer, adding balance to the round features; and avoid rimless frames, round frames and small frames that will accentuate the roundness of the face; 2) for oval shaped faces, select frames that have a strong bridge, are wider than the broadest part of the face and are geometric in shape; and avoid frames that are overlarge and cover up more than half of the face as they will throw off the natural balance and symmetry of the oval face; 3) for square shaped faces, select oval or round frames that soften the angularity and sit high on the bridge of the nose to balance and add a thinner appearance to the angles of a square face; 4) for diamond shaped faces, select frames that frames what sweep up or are wider than the cheekbones, such as cat eye glasses and oval frames; and 5) for heart-shaped faces, select frames that balance the width of the forehead with the narrowness of the chin such as, but not limited to, frames having low-set temples and bottom heavy frame lines that will add width to that narrower part of your face, and round or square frames with curved edges that will help draw attention away from a broad, high forehead.

Other facial attributes may include nose size and shape, eyes size and shape, interpupillary distance, and temple length. In one embodiment, the process is configured to multiply eye size by 2 then add the bridge size to determine a total width. In one embodiment, the recommended frames will be within ±1 to 2 mm of the total width. Another facial attribute may be the back vertex distance (BVD), which specifies the distance between the back of the spectacle lens and the front surface of the eye. This attribute is important in higher prescriptions, usually above ±4.00 D, as slight changes in the distance between the spectacles and the eyes above this level can cause the patient to perceive a different power, leading to blur and/or other symptoms. Thus, in certain embodiments, for higher prescriptions, the process will only recommend frames that provide the appropriate BVD.

In some embodiments, the frames set 404 may consist of one frame that provides the optimum viewing correction for the patient. In other embodiments, the frames set 404 may include a plurality of frames that satisfy all, the most, or a preferred combination of specified attributes. In some embodiments, the set of frames at frames set 406 may be further reduce by applying one or more filters to frames set 406 based on one or more user selected criteria, such as, but not limited to, color, brand, cost, material, flexibility, availability, full rim, semi-rimless, rimless, and raised or flat nose pads to generate frames set 408.

Figure 5:
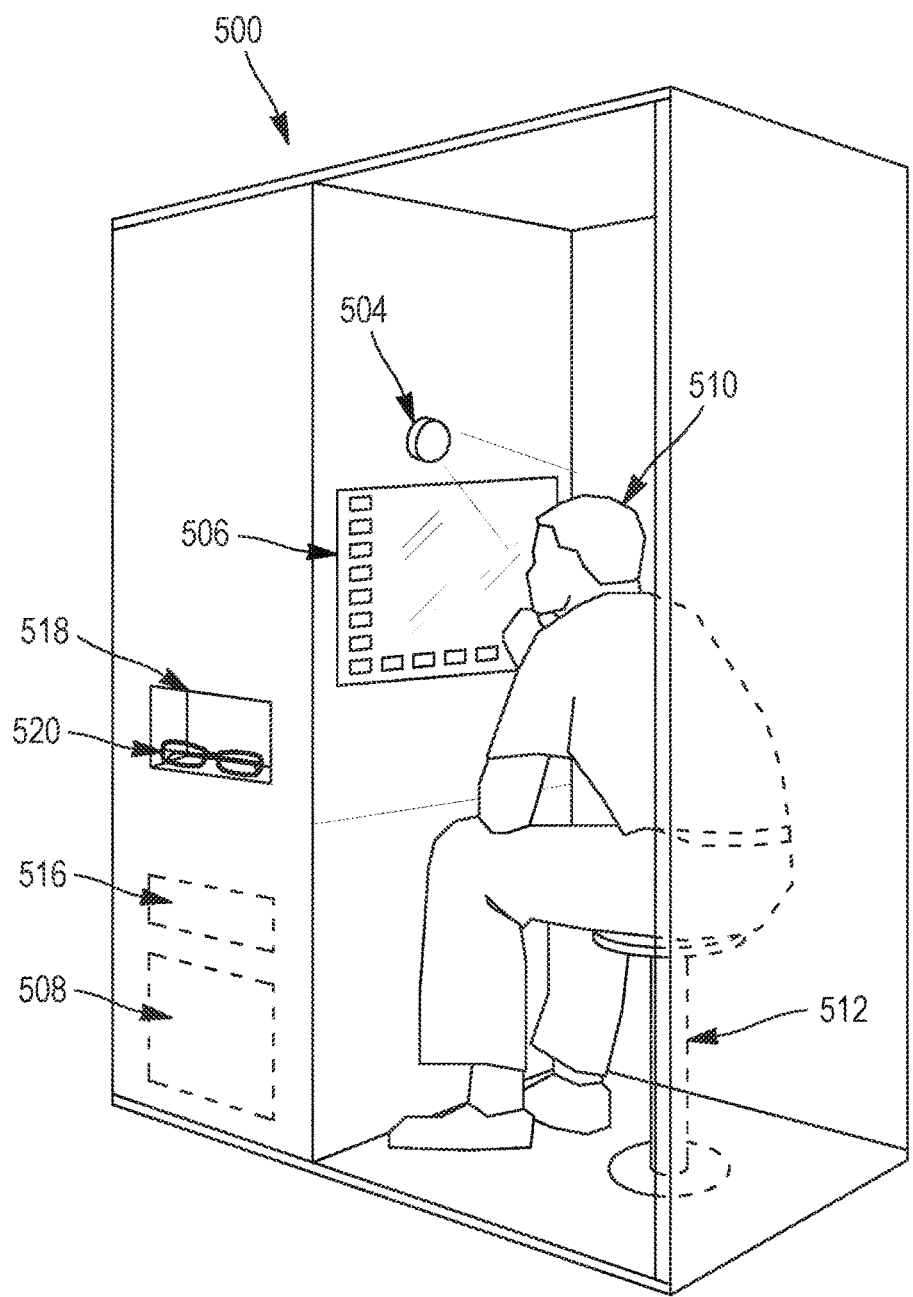
FIG. 5 is a block diagram illustrating a frame recommendation system 500 in accordance with one embodiment.

FIG. 5 is a block diagram illustrating a frame recommendation system 500 in accordance with one embodiment. In one embodiment, the frame recommendation system 500 may be an enclosed structure such as, but not limited to, a booth, kiosk, or a small room that has a door or curtain as an opening for enabling entry. In other embodiments, the frame recommendation system 500 may be completely open and not enclosed by any particular structure.

In the depicted embodiment, the frame recommendation system 500 includes one or more cameras and/or image scanners 504, such as, but not limited to a 3D laser scanner for capturing image(s) of a patient/user 510 for determining the facial attributes of the patient 510. The one or more cameras and/or image scanners 504 may be placed in various locations of the frame recommendation system 500 including the top and lateral sides of the frame recommendation system 500. In some embodiments, the frame recommendation system 500 may include computer executable instructions for automatically rotating, changing the angle of, or moving one or more the cameras and/or image scanners 504 to a different location for capturing the desired images or scans for determining the facial attributes of the patient.

In certain embodiments, the frame recommendation system 500 also includes a user interface 506 for receiving user input and/or displaying information such as, but not limited to, the at least one recommended frame. For instance, the user interface 506 may include a mouse, keyboard, monitor, and/or touchscreen display. The frame recommendation system 500 would also include electrical components 508 such as, but not limited to, a processor and memory as described above.

In this particular embodiment, the frame recommendation system 500 includes a seating apparatus 512 such as a chair or bench for the patient 510. In one embodiment, the frame recommendation system 500 may include computer executable instructions for automatically rotating, moving, and/or changing the angle of the seating apparatus 512 for capturing the desired images of the patient. The frame recommendation system 500 may also include computer executable instructions for automatically adjusting the height of the seating apparatus 512 based on a height of the patient 510. In some embodiments, the height of the patient 510 may be manually entered using the user interface 506 and/or may be automatically retrieved from an electronic patient file.

Also in this embodiment, the frame recommendation system 500 includes an integrated or coupled fabrication device 516, such as, but not limited to, a 3D printer for fabricating the at least one of the recommended frames and/or frame and lens combination 520. Currently, 3D printing is a form of additive manufacturing that creates an object by adding material to the object layer by layer based on a set of computer instructions or a computer file such as, but not limited to, a standard tessellation language (STL) file. Non-limiting examples of 3D printing technology include direct 3-D printing, which dispenses thick waxes and plastic polymers that solidify to form each new cross-section of a sturdy 3D object. Other 3D printing technology includes binder 3-D printing, fused deposition modeling (FDM), photopolymerization and rapid prototyping (RP). In certain embodiments, other methods for fabricating a recommended frame may be employed. For example, instead of adding layers, in some embodiments, the fabrication process may remove material from an existing block based on a set of computer instructions or a computer file.

In one embodiment, the frame recommendation system 500 may locally store in memory the computer files or instructions that enable the system to fabricate any recommended frame. Alternatively, if a particular selected frame file is not stored locally, in certain embodiments, the frame recommendation system 500 may be configured to retrieve the frame file from an external source such as, but not limited to, the frames database 120, a vendor system, third party system, a manufacturer or owner of the frame design, or from performing a general query on the Internet or other network.

Once the frame recommendation system 500 has the instructions for generating a recommended frame, the actual fabrication process may begin. In one embodiment, the frame recommendation system 500 will include one or more receptacles that hold the needed polymers, binders and other consumables that are used in fabricating a recommended frame. The disclosed embodiments envision that based on technological advances, the frames may be generated during the same visit and that the patient would be able to receive a complete pair of glasses within minutes of selecting a recommended frame. The patient or a technician/physician may retrieve the frame and lens combination 520 from a dispenser 518 once it is done printing. In certain embodiments, the frame recommendation system 500 may also be used to print a non-recommended frame, e.g., a frame that the patient really likes, but is not recommended by the frame recommendation system 500 as it did not meet one or more of the specified criteria.

Accordingly, the disclosed embodiments provide a technical solution to the problems associated with improper frame selection such as, but not limited to, the improper selection of frames that do not provide the optimum visual correction to a patient and the misuse of time in selecting frames that will not work with a particular prescription. Further, the disclosed embodiments provide a teaching tool that enhances the patient's understanding of the reasons a particular frame is recommended.

Although representative processes and articles have been described in detail herein, those skilled in the art will recognize that various substitutions and modifications may be made without departing from the scope of what is described and defined by the appended claims. For instance, although the above description describes particular steps and functions being performed in a certain order and by particular modules, the features disclosed herein are not intended to be limited to any particular order or any particular implementation constraint. For example, in FIG. 5, the patient attributes may be applied prior to the lens attributes being applied for generating the subset of frames. Further, one or more modules may be added, deleted, and/or combined in the embodiment described in FIG. 3. Therefore, it is to be understood that the invention is not to be limited to the specific embodiments disclosed.

Additionally, although specific terms are employed herein, they are used in a generic and descriptive sense only and not for purposes of limitation. For instance, the term database, as used herein, is intended to include any form of organized data, including, but not limited to, data found in tables, charts, spreadsheets, and documents. Furthermore, the term database does not imply the use of a particular or specialized database software nor does it imply the use of any particular data structure.

In addition, as used herein, the term "attribute" means a quality or characteristic. The term "attributes" means one or more attributes.

In summary, the disclosed embodiments include an optimizing frame recommendation system, method, and computer program product. In addition to the embodiments described above, many examples of specific combinations are within the scope of the disclosure, some of which are detailed below.

EXAMPLE 1

A system comprising: a processor for executing computer-executable instructions and a computer-readable storage media having stored thereon computer-executable instructions for receiving prescription data of a patient for corrective lenses; receiving image data associated with a face of the patient; determining lens attributes for the patient based upon the prescription data of the patient; determining facial attributes from the image data of the patient; and determining at least one frame recommendation for the patient based upon the lens attributes and the facial attributes of the patient.

EXAMPLE 2

A system comprising: a processor for executing computer-executable instructions and a computer-readable storage media having stored thereon computer-executable instructions for receiving prescription data of a patient for corrective lenses; receiving image data associated with a face of the patient, wherein receiving the image data associated with the face of the patient comprises receiving a frontal image and at least one lateral image of the patient; determining lens attributes for the patient based upon the prescription data of the patient; determining facial attributes from the image data of the patient; and determining at least one frame recommendation for the patient based upon the lens attributes and the facial attributes of the patient.

EXAMPLE 3

A system comprising: a processor for executing computer-executable instructions and a computer-readable storage media having stored thereon computer-executable instructions for receiving prescription data of a patient for corrective lenses; receiving image data associated with a face of the patient; determining lens attributes for the patient based upon the prescription data of the patient; determining facial attributes from the image data of the patient; determining at least one frame recommendation for the patient based upon the lens attributes and the facial attributes of the patient; and outputting frame dimensions of the at least one frame recommendation.

EXAMPLE 4

A system comprising: a processor for executing computer-executable instructions and a computer-readable storage media having stored thereon computer-executable instructions for receiving prescription data of a patient for corrective lenses; receiving image data associated with a face of the patient; determining lens attributes for the patient based upon the prescription data of the patient; determining facial attributes from the image data of the patient; and querying a remote database containing frame information to determine at least one frame recommendation for the patient based upon the lens attributes and the facial attributes of the patient.

EXAMPLE 5

A system comprising: a processor for executing computer-executable instructions and a computer-readable storage media having stored thereon computer-executable instructions for receiving prescription data of a patient for corrective lenses; receiving image data associated with a face of the patient; determining lens attributes for the patient based upon the prescription data of the patient; determining facial attributes from the image data of the patient; determining at least one frame recommendation for the patient based upon the lens attributes and the facial attributes of the patient; and filtering the at least one frame recommendation based on at least one frame criteria.

EXAMPLE 6

A system comprising: a processor for executing computer-executable instructions and a computer-readable storage media having stored thereon computer-executable instructions for receiving prescription data of a patient for corrective lenses; receiving at least one patient attribute; receiving image data associated with a face of the patient; determining lens attributes for the patient based upon the prescription data of the patient; determining facial attributes from the image data of the patient; and determining at least one frame recommendation for the patient based upon the lens attributes, the at least one patient attribute, and the facial attributes of the patient.

EXAMPLE 7

A computer implemented method for determining at least one frame recommendation for a patient, the method comprising: receiving prescription data of a patient for corrective lenses; receiving image data associated with a face of the patient; determining lens attributes for the patient based upon the prescription data of the patient; determining facial attributes from the image data of the patient; and determining at least one frame recommendation for the patient based upon the lens attributes and the facial attributes of the patient.

EXAMPLE 8

A computer-readable storage media having stored thereon computer-executable instructions, that when executed by a processor of a system, enables the system to: receive prescription data of a patient for corrective lenses; receive image data associated with a face of the patient; determine lens attributes for the patient based upon the prescription data of the patient; determine facial attributes from the image data of the patient; and determine at least one frame recommendation for the patient based upon the lens attributes and the facial attributes of the patient.

The above specific example embodiments are not intended to limit the scope of the claims. The example embodiments may be modified by including, excluding, or combining one or more features or functions described in the disclosure such as, but not limited to:

including a fabrication device and fabricating a selected frame from the at least one frame recommendation using the fabrication device.

initiating a transaction to purchase a selected frame from the at least one frame recommendation.

billing at least a portion of the transaction to an insurer of the patient.

generating an image of the at least one frame recommendation for the patient.

generating an image of the patient wearing a selected frame from the at least one frame recommendation.

querying the frame database by specifying as query inputs specific frame dimensions or a range of frame dimensions.

The scope of the claims is intended to broadly cover the disclosed embodiments and any such modification or combinations as disclosed herein.

What is claimed is:

1. A system comprising:
   one or more of at least one camera and at least one image scanner;
   a display;
   a processor for executing computer-executable instructions;
   a computer-readable storage media having stored thereon computer-executable instructions for:
     receiving prescription data of a patient for corrective lenses input into the system from a user at a user interface or imported into the system by another system,
     receiving information relative to a lifestyle of the patient,
     controlling one or more of the at least one camera and the at least one image scanner by a facial contour image module to capture image data associated with a face of the patient from the one or more of the at least one camera and the at least one image scanner,
     determining lens attributes for the patient based upon the prescription data of the patient, the lens attributes being physical features of the lens,
     determining facial attributes using the facial image contour module to analyze features of the patient from the captured image data of the patient obtained by the one or more of the at least one camera and the at least one image scanner,
     determining a first subset of frames of a plurality of frames based on the determined lens attributes,
     determining a second subset of frames of the plurality of frames based on the determined facial attributes, the second subset of frames having frame dimensions satisfying ranges corresponding to measurements of the facial attributes,
     determining a third subset of frames of the plurality of frames based on the information relative to the lifestyle of the patient,
     filtering the plurality of frames to obtain at least one frame recommendation of at least one frame for the patient, the at least one frame being within the determined first subset of frames, the determined second subset of frames, and the determined third subset of frames, and
     outputting the at least one frame recommendation for the patient to the display by one of: (i) displaying the at least one frame recommendation as a two-dimensional image on the display, (ii) displaying the at least one frame recommendation as a three-dimensional rotatable image on the display, (iii) displaying the at least one frame recommendation on an image of the patient, (iv) displaying the at least one frame recommendation on images of other people other than the patient that have similar facial attributes as the patient, and (v) outputting a fabricated frame of the at least one frame recommendation.

2. The system of claim 1, wherein the receiving the image data associated with the face of the patient comprises receiving a frontal image and at least one lateral image of the patient.

3. The system of claim 1, wherein the outputting the at least one frame recommendation for the patient comprises outputting frame dimensions of the at least one frame recommendation.

4. The system of claim 1, wherein the obtaining the at least one frame recommendation for the patient comprises querying a remote database containing frame information.

5. The system of claim 1, wherein the computer-readable storage media further stores thereon computer-executable instructions for filtering the at least one frame recommendation based on at least one frame criteria.

6. The system of claim 1, wherein the computer-readable storage media further stores thereon computer-executable instructions for receiving at least one patient attribute, and
wherein the determining the lens attributes and the determining the at least one frame recommendation are further based upon the at least one patient attribute.

7. The system of claim 1, further comprising a three-dimensional printer,
wherein the computer-readable storage media further stores thereon computer-executable instructions for printing a selected frame from the at least one frame recommendation using the three-dimensional printer.

8. The system of claim 1, wherein the computer-readable storage media further stores thereon computer-executable instructions for initiating a transaction to purchase a selected frame from the at least one frame recommendation.

9. The system of claim 8, wherein the computer-readable storage media further stores thereon computer-executable instructions for billing at least a portion of the transaction to an insurer of the patient.

10. A computer-implemented method for determining at least one frame recommendation for a patient, the method comprising:
receiving prescription data of a patient for corrective lenses input into a frame recommendation system from a user at a user interface or imported into the frame recommendation system by another system;
receiving information relative to a lifestyle of a patient or to statistical data associated with one or more of a height and a weight of the patient;
controlling one or more of at least one camera and at least one image scanner by a facial contour image module to capture image data associated with a face of the patient from one or more of the at least one camera and the at least one image scanner;
determining, using a processor, lens attributes for the patient based upon the prescription data of the patient, the lens attributes being physical features of the lens;
determining facial attributes using the facial image contour module to analyze features of the patient from the captured image data of the patient obtained by the one or more of the at least one camera and the at least one image scanner;
determining a first subset of frames of a plurality of frames based on the determined lens attributes;
determining a second subset of frames of the plurality of frames based on the determined facial attributes, the second subset of frames having frame dimensions satisfying ranges corresponding to measurements of the facial attributes;
determining a third subset of frames of the plurality of frames based on the information relative to the lifestyle of the patient or to the statistical data;
determining at least one frame recommendation for the patient based upon the first subset of frames, the second subset of frames, and the third subset of frames;
filtering the plurality of frames to obtain at least one frame recommendation of at least one frame for the patient, the at least one frame being within the determined first subset of frames, the determined second subset of frames, and the determined third subset of frames; and
outputting the at least one frame recommendation for the patient by one of: (i) displaying the at least one frame recommendation as a two-dimensional image on a display, (ii) displaying the at least one frame recommendation as a three-dimensional rotatable image on the display, (iii) displaying the at least one frame recommendation on an image of the patient, (iv) displaying the at least one frame recommendation on images of other people other than the patient that have similar facial attributes as the patient, and (v) outputting a fabricated frame of the at least one frame recommendation.

11. A computer-implemented method for determining at least one frame recommendation for a patient, the method comprising:
receiving prescription data of a patient for corrective lenses input into a frame recommendation system from a user at a user interface or imported into the frame recommendation system by another system;
receiving information relative to a lifestyle of a patient or to statistical data associated with one or more of a height and a weight of the patient;
controlling one or more of at least one camera and at least one image scanner by a facial contour image module to capture image data associated with a face of the patient from one or more of the at least one camera and the at least one image scanner;
determining, using a processor, lens attributes for the patient based upon the prescription data of the patient, the lens attributes being physical features of the lens;
determining facial attributes using the facial image contour module to analyze features of the patient from the captured image data of the patient obtained by the one or more of the at least one camera and the at least one image scanner;
determining a first subset of frames of a plurality of frames based on the determined lens attributes;
determining a second subset of frames of the plurality of frames based on the determined facial attributes, the second subset of frames having frame dimensions satisfying ranges corresponding to measurements of the facial attributes;
determining a third subset of frames of the plurality of frames based on the information relative to the lifestyle of the patient or to the statistical data;
determining at least one frame recommendation for the patient based upon the first subset of frames, the second subset of frames, and the third subset of frames;
filtering the plurality of frames to obtain at least one frame recommendation of at least one frame for the patient, the at least one frame being within the determined first subset of frames, the determined second subset of frames, and the determined third subset of frames; and fabricating a selected frame from the at least one frame recommendation using an integrated fabrication device.

12. The computer-implemented method of claim 10, further comprising:
querying a database containing frame information; and
filtering the at least one frame recommendation based on at least one frame criteria.

13. The computer-implemented method of claim 12, wherein the querying the database containing frame information includes specifying as query inputs specific frame dimensions.

14. A computer-readable storage media having stored thereon computer-executable instructions, that when executed by a processor of a system, enables the system to:
receive prescription data of a patient for corrective lenses input into the system from a user at a user interface or imported into the system by another system;
receive information relative to a lifestyle of a patient or to statistical data associated with one or more of a height and a weight of the patient,
control one or more of at least one camera and at least one image scanner by a facial contour image module to capture image data associated with a face of the patient;
determine lens attributes for the patient based upon the prescription data of the patient, the lens attributes being physical features of the lens;
determine facial attributes using the facial image contour module to analyze features of the patient from the captured image data of the patient obtained by one or more of the at least one camera and the at least one image scanner;
determine a first subset of frames of a plurality of frames based on the determined lens attributes;
determine a second subset of frames of the plurality of frames based on the determined facial attributes, the second subset of frames having frame dimensions satisfying ranges corresponding to measurements of the facial attributes;
determine a third subset of frames of the plurality of frames based on the information relative to the lifestyle of the patient or to the statistical data;
determine at least one frame recommendation for the patient based upon the first subset of frames, the second subset of frames, and the third subset of frames;
filter the plurality of frames to obtain at least one frame recommendation of at least one frame for the patient, the at least one frame being within the determined first subset of frames, the determined second subset of frames, and the determined third subset of frames; and
output the at least one frame recommendation for the patient by one of: (i) displaying the at least one frame recommendation as a two-dimensional image on a display, (ii) displaying the at least one frame recommendation as a three-dimensional rotatable image on the display, (iii) displaying the at least one frame recommendation on an image of the patient, (iv) displaying the at least one frame recommendation on images of other people other than the patient that have similar facial attributes as the patient, and (v) outputting a fabricated frame of the at least one frame recommendation.

15. The computer-readable storage media of claim 14, wherein the computer-executable instructions when executed by the processor of the system further enable the system to fabricate a selected frame from the at least one frame recommendation using an integrated fabrication device.

16. A system comprising:
one or more of at least one camera and at least one image scanner;
a processor for executing computer-executable instructions;
a computer-readable storage media having stored thereon computer-executable instructions for:
receiving prescription data of a patient for corrective lenses input into the system from a user at a user interface or imported into the system by another system,
receiving statistical data associated with one or more of a height and a weight of the patient,
controlling one or more of at least one camera and at least one image scanner by a facial contour image module to capture image data associated with a face of the patient from the one or more of the at least one camera and the at least one image scanner,
determining lens attributes for the patient based upon the prescription data of the patient, the lens attributes being physical features of the lens,
determining facial attributes using the facial image contour module to analyze features of the patient from the captured image data of the patient obtained by the one or more of the at least one camera and the at least one image scanner,
determining a first subset of frames of a plurality of frames based on the determined lens attributes,
determining a second subset of frames of the plurality of frames based on the determined facial attributes, the second subset of frames having frame dimensions satisfying ranges corresponding to measurements of the facial attributes,
determining a third subset of frames of the plurality of frames based on the statistical data,
determining at least one frame recommendation for the patient based upon the first subset of frames, the second subset of frames, and the third subset of frames,
filtering the plurality of frames to obtain at least one frame recommendation of at least one frame for the patient, the at least one frame being within the determined first subset of frames, the determined second subset of frames, and the determined third subset of frames, and
outputting the at least one frame recommendation for the patient by one of: (i) displaying the at least one frame recommendation as a two-dimensional image on a display, (ii) displaying the at least one frame recommendation as a three-dimensional rotatable image on the display, (iii) displaying the at least one frame recommendation on an image of the patient, (iv) displaying the at least one frame recommendation on images of other people other than the patient that have similar facial attributes as the patient, and (v) outputting a fabricated frame of the at least one frame recommendation.

17. The system of claim 16, wherein the receiving the image data associated with the face of the patient comprises receiving a frontal image and at least one lateral image of the patient.

18. The system of claim 16, wherein the determining the at least one frame recommendation for the patient comprises outputting frame dimensions of the at least one frame recommendation.

19. The system of claim 16, wherein the determining the at least one frame recommendation for the patient comprises querying a remote database containing frame information.

20. The system of claim 16, further comprising a three-dimensional printer,
   wherein the computer-readable storage media further stores thereon computer-executable instructions for printing a selected frame from the at least one frame recommendation using the three-dimensional printer.

* * * * *